United States Patent [19]

Bosies et al.

[11] Patent Number: 4,666,895

[45] Date of Patent: May 19, 1987

[54] DIPHOSPHONIC ACID DERIVATIVES

[75] Inventors: Elmar Bosies, Weinheim; Rudi Gall, Hirschberg, both of Fed. Rep. of Germany

[73] Assignee: Boehringer Mannheim GmbH, Mannheim, Fed. Rep. of Germany

[21] Appl. No.: 846,250

[22] Filed: Mar. 31, 1986

[30] Foreign Application Priority Data

Apr. 6, 1985 [DE] Fed. Rep. of Germany ....... 3512536

[51] Int. Cl.$^4$ .................... C07F 9/38; A61K 31/045; A61K 31/16; A61K 31/66
[52] U.S. Cl. ................ 514/108; 260/502.5 C; 546/22; 548/112; 548/119; 548/413; 548/414
[58] Field of Search ................ 260/502.5 C; 514/108; 558/159; 546/22; 548/112, 119, 413, 414

[56] References Cited

U.S. PATENT DOCUMENTS

| | | | |
|---|---|---|---|
| 3,899,496 | 8/1975 | Schindler et al. | 546/22 |
| 3,979,385 | 9/1976 | Wallmann et al. | 546/22 |
| 4,029,697 | 6/1977 | Krueger et al. | 260/502.5 C |
| 4,134,969 | 1/1979 | Schmidt-Dunker | 514/108 |
| 4,239,695 | 12/1980 | Chai et al. | 546/22 |
| 4,503,049 | 3/1985 | Biere et al. | 548/119 |

FOREIGN PATENT DOCUMENTS

| | | | |
|---|---|---|---|
| 0000061 | 12/1978 | European Pat. Off. | 558/159 |
| 2118042 | 10/1983 | United Kingdom | 260/502.4 P |

*Primary Examiner*—J. E. Evans
*Attorney, Agent, or Firm*—Felfe & Lynch

[57] ABSTRACT

The present invention provides diphosphonic acid derivatives of the general formula:

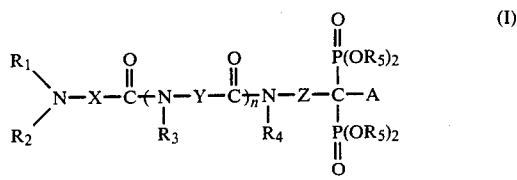

wherein $R_1$, $R_2$, $R_3$, $R_4$ and $R_5$, independently of one another or also together, signify hydrogen atoms or lower alkyl radicals, whereby $R_1$ and X or $R_3$ and Y or $R_4$ and Z, together with the nitrogen atom to which they are attached, can form a five- or six-membered ring, X and Y, which can be the same or different, represent a straight-chained or branched alkylene chain with up to 6 carbon atoms which can optionally be substituted by aromatic or heteroaromatic radicals, Z is a straight-chained or branched alkylene chain with up to 6 carbon atoms, which can be interrupted by heteroatoms and can optionally also be substituted by aromatic or heteroaromatic radicals, n is 0, 1 or 2 and A is a hydrogen atom or a hydroxyl group, and the pharmacologically acceptable salts thereof. The present invention also provides processes for the preparation of these new diphosphonic acid derivatives and pharmaceutical compositions containing them for the treatment of calcium metabolism disturbances.

18 Claims, No Drawings

DIPHOSPHONIC ACID DERIVATIVES

The present invention is concerned with new diphosphonic acid derivatives, processes for the preparation thereof as well as pharmaceutical compositions containing them.

Federal Republic of Germany patent specification No. 18 13 659 describes diphosphonic acid derivatives, of which 1-hydroxyethane-1,1-diphosphonic acid has achieved importance for the treatment of Paget's disease. In Belgium patent specification No. 896,453A, as well as in European patent specification No. 0,096,931 A, there are described aminoalkane-1,1-diphosphonic acids as good calcium complex formers which can also be used for the treatment of increased bone resorption. However, such substances are extremely poorly resorbed.

Consequently, there is a need to find aminoalkane-diphosphonates with an improved resorption.

We have now found that analogues of these compounds, in which the nitrogen atom is acylated by amino acids or by di- or tripeptides, are substantially better resorbed and, as equally good calcium complex formers, are suitable for the wider treatment of calcium metabolism disturbances. In particular, they can be used in cases where the formation and breakdown of bone is disturbed, for example in cases of osteoporosis, Paget's disease, Bechterew's disease and the like. On the basis of these properties, they can, however, also be used in the therapy of bone metastases, of urolithiasis and for the prevention of hetertopic ossification. Due to their influencing of the calcium metabolism, they also form a basis for the treatment of rheumatoid arthritis, osteoarthritis and degenerative arthrosis.

Thus, according to the present invention, there are provided diphosphonates of the general formula:

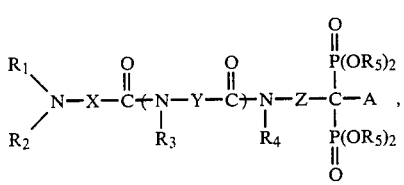

wherein $R_1$, $R_2$, $R_3$, $R_4$ and $R_5$, independently of one another or also together, are hydrogen atoms or lower alkyl radicals, whereby $R_1$ and X or $R_3$ and Y or $R_4$ and Z, together with the nitrogen atom to which they are attached, can form a five- or six-membered ring, X and Y, which can be the same or different, are straight-chained or branched alkylene chains containing up to 6 carbon atoms which can optionally be substituted by aromatic or heteroaromatic radicals, Z is a straight-chained or branched alkylene chain containing up to 6 carbon atoms which can be interrupted by heteroatoms and can optionally also be substituted by aromatic or heteroaromatic radicals, n is 0, 1 or 2 and A is a hydrogen atom or a hydroxyl group, and the pharmacologically acceptable salts thereof.

Lower alkyl radicals in the case of the substituents $R_1$–$R_5$ and in the case of the hereinafter mentioned radicals $R_6$–$R_{11}$ in the described process variants mean alkyl radicals containing up to 4 carbon atoms, methyl, ethyl and isopropyl radicals being preferred.

$R_5$ is preferably a hydrogen atom.

Amongst the aromatic and heteroaromatic radicals mentioned as substituents in the case of the radicals X, Y and Z, there are preferably to be understood the phenyl, imidazolyl and indolyl radicals.

Preferred heteroatoms in the radical Z are, in particular, oxygen and sulphur, and n is preferably 0 or 1.

As a rule, the radicals $(R_1R_2)N$—X—CO— and

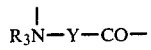

are common amino acid residues, for example of glycine, alanine, β-alanine, valine, leucine, isoleucine, lysine, glutamine, sarcosine and arginine, the preferred residues being those of glycine, alanine and leucine, these residues possibly being substituted by $R_1$, $R_2$ and $R_3$.

If $(R_1R_2)$ N—X—CO—and/or $R_3N$—Y—CO—form a ring, these radicals preferably represent the proline residue. When $R_4$ and Z, together with the nitrogen atom to which they are attached, form a five- or six-membered ring, these residues can represent a 2-pyrrolidinyl, 3-pyrrolidinyl or piperidinyl radical, the 4-piperidinyl radical being preferred.

When n is 1 or 2, the radical $(R_1R_2)N$—X—CO—(N—$R_3$—Y—CO)$_n$—preferably represents one of the following radicals: Gly-Gly-, Ala-Ala-, Gly-Ala-, Ala-Gly-, Gly-Gly-Gly- or Ala-Ala-Ala-.

Asymmetric carbon atoms present in X, Y or Z can have the R-, S- or R,S-configuration.

Compounds of general formula (I) are prepared by known processes and preferably by (a) reacting a diphosphonate of the general formula:

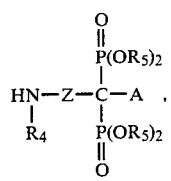

in which $R_4$, $R_5$, Z and A have the above-given meanings and in which nitrogen atoms possibly present in the Z radical are protected, with an activated carboxylic acid of the general formula:

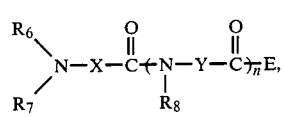

in which X, Y and n have the above-given meanings and nitrogen atoms possibly present in these radicals are protected, $R_6$, $R_7$ and $R_8$ are lower alkyl radicals or protective groups common in peptide chemistry or $R_6$ and $R_7$ can together also form a phthaloyl radical and $R_6$ and X, as well as $R_8$ and Y, together with the nitrogen atom to which they are attached, can form a five- or six-membered ring and E is a hydroxyl group or an activating group common in peptide chemistry, whereafter the protective groups present are split off; or (b) reacting a compound of the general formula:

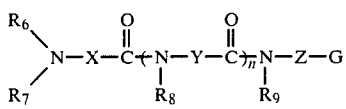 (IV)

in which X, Y, Z and n have the above-given meanings and nitrogen atoms possibly present in these radicals are protected, $R_6$, $R_7$, $R_8$ and $R_9$ are hydrogen atoms, lower alkyl radicals or protective groups common in peptide chemistry, whereby $R_6$ and $R_7$ can together also form a phthaloyl radical and $R_6$ and X, $R_8$ and Y, as well as $R_9$ and Z, together with the nitrogen atom to which they are attached, can form a five- or six-membered ring, and G signifies the group —CO—Hal, wherein Hal is bromine or chlorine, or a reactive residue, for example a halogen atom or a sulphonate group, in the case in which G is a —CO—Hal group, with a trialkyl phosphite of the general formula:

 (V), in which $R_{10}$ is a lower alkyl radical, to give an acyl phosphonate of the general formula:

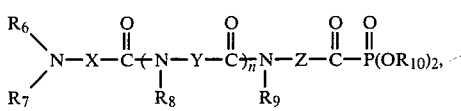 (VI)

in which X, Y, Z, n, $R_6$, $R_7$, $R_8$, $R_9$ and $R_{10}$ have the above-given meanings, and subsequently with a dialkyl phosphite of the general formula:

 (VII)

in which $R_{11}$ is a lower alkyl radical, to give a diphosphonate of the general formula:

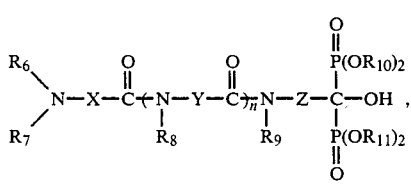 (VIII)

in which X, Y, Z, n, $R_6$, $R_7$, $R_8$, $R_9$, $R_{10}$ and $R_{11}$ have the above-given meanings, or, in the case in which G is the above-mentioned reactive group, with a compound of the general formula:

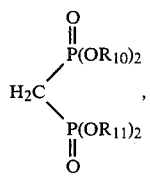 (IX)

in which $R_{10}$ and $R_{11}$ have the above-given meanings, to give a diphosphonate of the general formula:

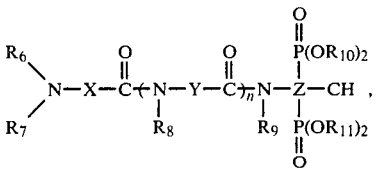 (X)

in which X, Y, Z, n, $R_6$, $R_7$, $R_8$, $R_9$, $R_{10}$ and $R_{11}$ have the above-given meanings, splitting off the protective groups possibly present and, if desired, saponifying the resultant tetraesters to diesters or acids of general formula (I).

The protective groups used in the above-described processes are known from peptide chemistry and are described in detail in, for example, Houben-Weyl, Volume 15/1. Preferred protective groups include aralkyloxycarbonyl radicals, especially the benzyloxycarbonyl radical, or alkoxycarbonyl radicals, preferably the tert.-butoxycarbonyl radical. However, there can also be used, for example, formyl, trityl, trifluoroacetyl or trichloroethoxycarbonyl radicals.

The splitting off of the protective groups after the reaction has taken place is carried out in the usual manner. Benzyloxycarbonyl and trityl radicals can be split off by catalytic hydrogenation in the presence of noble metal catalysts, for example palladium on charcoal, and tert.-butoxycarbonyl radicals by the action of strong acids, for example hydrochloric acid or trifluoroacetic acid. Trichloroethoxycarbonyl radicals can be split off reductively, for example by the action of zinc in acetic acid. The phthaloyl radical can be removed in an acidic medium or also by hydrazonolysis.

The —CO—E grouping present in the compound of general formula (III) used in process (a) can be a reactive derivative of a carboxylic acid. For this purpose, there can be used mixed anhydrides, especially with carbonic acid mono lower alkyl esters, such as ethyl or isobutyl esters, or active esters, especially p-nitrophenyl, 2,4,5-trichlorophenyl, N-hydroxysuccinimide or 1-N-hydroxybenzotriazole esters. If E is a hydroxyl group, the activation of the carboxyl group can be carried out according to the carbodiimide process.

The reactive residue G present in the compound of general formula (IV) used in process (b) is to be understood to be halogen, preferably the corresponding iodide or bromide, or a sulphonate, for example mesylate, benzenesulphonate or p-toluenesulphonate.

In the case of process (a) there are preferably used inert organic solvents, for example methylene chloride, acetone, acetonitrile, dimethylformamide, tetrahydrofuran or dioxan or mixtures of these solvents at temperatures of from $-70°$ to $+100°$ C. and preferably of from $-30°$ to $+20°$ C. If, in the case of the reaction, the phosphonic acid groups are protected by salt formation, then the reaction is preferably carried out in an aqueous medium, possibly with the addition of an alcohol or etherified diol, for example dimethoxyethane, or in a two-phase system, for example water/methylene chloride, when, as reactive derivative of the compound of general formula (III), there is used a carboxylic acid halide, a mixed anhydride or an active ester, preferably a N-hydroxysuccinimide ester.

In the case of process (b), when G is a —CO—Hal radical, the acid chloride of general formula (IV) is allowed to react with the trialkyl phosphite of general formula (V) at a temperature of from $0°$ to $+80°$ C. and preferably of from 20° to 40° C. It is possible to work without the use of a solvent or also in the presence of an inert solvent, for example diethyl ether, tetrahydrofuran, dioxan or also a halogenated hydrocarbon, for example methylene chloride. The acyl phosphonate of general formula (VI) formed as intermediate product can be isolated or further reacted directly. The subsequent reaction is carried out in the presence of a weak base, preferably a secondary amine, for example dibutylamine, at a temperature of from 0° to +60° C. and preferably of from 10° to 30° C. When G in the compound of general formula (IV) is a reactive residue, for example halogen or sulphonate, the methylenediphosphonic ester of general formula (IX) is used in the form of its sodium or potassium salt. For this purpose, it is reacted with sodium or potassium or the corresponding hydride in an inert solvent, for example benzene, toluene or dimethylformamide. However, the alkali metal salt can also be produced by the action of an alkali metal alcoholate in the corresponding alcohol and the further reaction is carried out with this alcohol as solvent. The temperature used is hereby from 0° to +40° C. and preferably about 25° C. The alkali metal salt is reacted with the corresponding halide or sulphonate without isolation at a temperature of from 20° to 110° C.

The tetraalkyl esters possibly obtained in the case of processes (a) and (b) can be saponified to the diesters or to the free tetraacids. As a rule, the saponification to diesters takes place by treating the tetraalkyl esters with an alkali metal halide, preferably sodium iodide, in an appropriate solvent, for example acetone, at ambient temperature. There is thereby formed the symmetrical diester/disodium salt which can, if desired, be converted into the diester/diacid by means of an acidic ion exchanger. The conversion into free diphosphonic acids takes place, as a rule, by boiling with hydrochloric or hydrobromic acid. However, the splitting can also be carried out with a trimethylsilyl halide and preferably with a bromide or iodide. On the other hand, the free diphosphonic acids can again be converted into the tetraalkyl esters by boiling with orthoformic acid alkyl esters. The free diphosphonic acids of general formula (I) can be isolated as free acids or in the form of mono- or dialkali metal salts. As a rule, the alkali metal salts can be readily purified by reprecipitation from water/methanol or water/acetone.

As pharmacologically acceptable salts, there are especially preferred the alkali metal and ammonium salts which are prepared in the usual way, for example by neutralisation of the compounds with inorganic or organic bases, for example sodium or potassium hydrogen carbonate, aqueous sodium hydroxide solution, aqueous potassium hydroxide solution, aqueous ammonia or an amine, for example trimethylamine or triethylamine.

The new compounds of general formula (I) according to the present invention and the salts thereof can be administered enterally or parenterally in liquid or solid form. All the usual forms of administration can hereby be used, for example tablets, capsules, dragees, syrups, solutions, suspensions and the like. As injection medium, it is preferred to use water which contains the additives usual in the case of injection solutions, such as stabilising agents, solubilising agents and buffers. Additives of this kind include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Liquid carrier materials for injection solutions must be sterile and are preferably placed into ampoules.

Solid carrier materials include, for example, starch, lactose, mannitol, methyl cellulose, talc, highly dispersed silicic acids, high molecular weight fatty acids (such as stearic acid), gelatine, agaragar, calcium phosphate, magnesium stearate, animal and vegetable fats and solid high molecular weight polymers (such as polyethylene glycols). Compositions suitable for oral administration can, if desired, contain flavouring and sweetening materials.

The dosage can depend upon various factors, such as the mode of administration, species, age and/or individual state of health. The dosages to be administered daily are from about 1 to 1000 mg. in the case of humans and preferably from 10 to 200 mg. and can be taken one or more times divided up into smaller dosages.

Preferred compounds according to the present invention are, apart from the compounds mentioned in the following Examples and the compounds derivable by combination of all the meanings given in the claims, also the following diphosphonates:

2-(N-glycyl)-aminoethane-1-hydroxy-1,1-diphosphonic acid 2-(N-L-alanyl)-aminoethane-1-hydroxy-1,1-diphosphonic acid 2-(N-L-prolyl)-aminoethane-1-hydroxy-1,1-diphosphonic acid 2-(N-sarcosyl)-aminoethane-1-hydroxy-1,1-diphosphonic acid 2-(N-L-valyl)-aminoethane-1-hydroxy-1,1-diphosphonic acid 2-(N-glycylglycyl)-aminoethane-1-hydroxy-1,1-diphosphonic acid 1-hydroxy-1-[(N-glycyl)-piperidin-4-yl]-methane-1,1-diphosphonic acid 3-(N-L-leucyl)-aminopropane-1-hydroxy-1,1-diphosphonic acid 3-(N-lysyl)-aminopropane-1-hydroxy-1,1-diphosphonic acid 3-(N-glycylglycyl)-aminopropane-1-hydroxy-1,1-diphosphonic acid 3-(N-alanylglycyl)-aminopropane-1-hydroxy-1,1-diphosphonic acid 3-(N-glycylglycylglycyl)-aminopropane-1-hydroxy-1,1-diphosphonic acid 4-(N-L-lysyl)-aminobutane-1-hydroxy-1,1-diphosphonic acid 4-(N-L-prolyl)-aminobutane-1-hydroxy-1,1-diphosphonic acid 4-(N-L-glutamyl)-aminobutane-1-hydroxy-1,1-diphosphonic acid 4-(N-L-alanylglycyl)-aminobutane-1-hydroxy-1,1-diphosphonic acid 4-(N-L-alanyl-L-alanyl)-aminobutane-1-hydroxy-1,1-diphosphonic acid 5-(N-L-valyl)-aminopentane-1-hydroxy-1,1-diphosphonic acid 5-(N-L-lysyl)-aminopentane-1-hydroxy-1,1-diphosphonic acid 5-(N-glycyl-L-alanyl)-aminopentane-1-hydroxy-1,1-diphosphonic acid 5-(N-L-alanyl-L-alanyl)-aminopentane-1-hydroxy-1,1-diphosphonic acid 5-(N-L-alanyl-L-alanyl-L-alanyl)-aminopentane-1-hydroxy-1,1-diphosphonic acid 6-(N-glycylglycyl)-aminohexane-1-hydroxy-1,1-diphosphonic acid 7-(N-L-alanyl)-aminoheptane-1-hydroxy-1,1-diphosphonic acid
7-(N-L-alanyl-L-alanyl)-aminoheptane-1-hydroxy-1,1-diphosphonic acid
R-2-(N-glycyl)-aminopropane-1-hydroxy-1,1-diphosphonic acid
R-2-(N-L-alanyl)-aminopropane-1-hydroxy-1,1-diphosphonic acid
R,S-2-(N-glycylglycyl)-aminopropane-1-hydroxy-1,1-diphosphonic acid
R,S-(N-L-alanylglycyl)-aminopropane-1-hydroxy-1,1-diphosphonic acid
S-2-(N-glycyl)-aminopropane-1-hydroxy-1,1-diphosphonic acid
S-2-(N-L-alanyl)-aminopropane-1-hydroxy-1,1-diphosphonic acid
R-4-(N-glycyl)-aminopentane-1-hydroxy-1,1-diphosphonic acid
S-4-(N-glycyl)-aminopentane-1-hydroxy-1,1-diphosphonic acid
R,S-4-(N-L-alanyl)-aminopentane-1-hydroxy-1,1-diphosphonic acid
R,S-4-(N-D-alanyl)-aminopentane-1-hydroxy-1,1-diphosphonic acid
R,S-4-(N-D,L-alanyl)-aminopentane-1-hydroxy-1,1-diphosphonic acid
R,S-4-(N-L-prolyl)-aminopentane-1-hydroxy-1,1-diphosphonic acid
R,S-4-(N-L-leucyl)-aminopentane-1-hydroxy-1,1-diphosphonic acid
R,S-4-(N-glycylglycyl)-aminopentane-1-hydroxy-1,1-diphosphonic acid
R,S-4-(N-L-alanyl-L-alanyl)-aminopentane-1-hydroxy-1,1-diphosphonic acid
R,S-4-(N-glycyl-L-alanyl)-aminopentane-1-hydroxy-1,1-diphosphonic acid
R,S-4-(N-L-alanylglycyl)-aminopentane-1-hydroxy-1,1-diphosphonic acid
R,S-4-(N-glycylglycylglycyl)-aminopentane-1-hydroxy-1,1-diphosphonic acid
R-5-(N-glycyl)-aminohexane-1-hydroxy-1,1-diphosphonic acid
S-5-(N-glycyl)-aminohexane-1-hydroxy-1,1-diphosphonic acid
R,S-5-(N-glycyl)-aminohexane-1-hydroxy-1,1-diphosphonic acid
R,S-5-(N-L-alanyl)-aminohexane-1-hydroxy-1,1-diphosphonic acid
R,S-5-(N-L-alanylglycyl)-aminohexane-1-hydroxy-1,1-diphosphonic acid
5-(N-glycyl)-amino-4-oxapentane-1-hydroxy-1,1-diphosphonic acid
6-(N-L-alanyl)-amino-4-oxahexane-1-hydroxy-1,1-diphosphonic acid
1-hydroxy-1-[(N-glycyl)-pyrrolidin-2-yl]-methane-1,1-diphosphonic acid
6-(N-glycyl)-amino-4-thiahexane-1-hydroxy-1,1-diphosphonic acid
2-benzyl-2-(N-glycyl)-aminoethane-1-hydroxy-1,1-diphosphonic acid
2-(N-glycyl)-amino-3-(4-imidazolyl)-propane-1-hydroxy-1,1-diphosphonic acid
2-(N-glycylglycyl)-amino-3-(4-imidazolyl)-propane-1-hydroxy-1,1-diphosphonic acid
2-(N-L-alanyl)-amino-3-(3-indoyl)-propane-1-hydroxy-1,1-diphosphonic acid
2-(N-L-alanyl-L-alanyl)-amino-3-(3-indoyl)-propane-1hydroxy-1,1-diphosphonic acid
3-(N-glycyl)-aminopropane-1,1-diphosphonic acid
3-(N-glycylglycyl)-aminopropane-1,1-diphosphonic acid
3-(N-L-alanyl)-aminopropane-1,1-diphosphonic acid
4-(N-glycyl)-aminobutane-1,1-diphosphonic acid
4-(N-L-alanyl)-aminobutane-1,1-diphosphonic acid
4-(N-L-prolyl)-aminobutane-1,1-diphosphonic acid
4-(N-glycyl-L-alanyl)-aminobutane-1,1-diphosphonic acid
5-(N-glycyl)-aminopentane-1,1-diphosphonic acid
5-(N-L-alanylglycyl)-aminopentane-1,1-diphosphonic acid
6-(N-glycyl)-aminohexane-1,1-diphosphonic acid
6-(N-L-alanyl)-aminohexane-1,1-diphosphonic acid
6-(N-glycyl)-amino-4-oxahexane-1,1-diphosphonic acid
6-(N-L-prolyl)-amino-4-thiahexane-1,1-diphosphonic acid
3-(N-glycyl-N-methyl)-aminopropane-1-hydroxy-1,1-diphosphonic acid
3-(N-L-alanyl-N-methyl)-aminopropane-1-hydroxy-1,1-diphosphonic acid
3-(N-D-alanyl-N-methyl)-aminopropane-1-hydroxy-1,1-diphosphonic acid
4-(N-L-alanyl-N-methyl)-aminobutane-1-hydroxy-1,1-diphosphonic acid
4-(N-D-alanyl-N-methyl)-aminobutane-1-hydroxy-1,1-diphosphonic acid
1-[(N-L-alanyl)-pyrrolidin-3-yl]-methane-1-hydroxy-1,1-diphosphonic acid.

The following Examples illustrate some of the process variants which can be used for the synthesis of the new compounds according to the present invention. The structure of these compounds has been confirmed by H- and P-NMR spectroscopy and the purity was determined by means of P-NMR spectroscopy, thin layer electrophoresis (cellulose, oxalate buffer, pH 4.0) and by means of carbon, hydrogen, nitrogen, phosphorus and sodium analyses. For the characterisation of the individual compounds, there are given the $M_{rel}$ values (relative mobility) referred to pyrophosphate ($M_{rel}=1.0$).

EXAMPLE 1

4-(Glycyl)-aminobutane-1-hydroxy-1,1-diphosphonic acid

4-N-(Glycyl)-aminobutane-1-hydroxy-1,1-diphosphonic 4 g. of the tetrasodium salt of 4-aminobutane-1-hydroxy-1,1-diphosphonic acid are dissolved in 40 ml. water and mixed portionwise at ambient temperature, while stirring, with 4 g. phthaloylglycyl chloride. The pH value of the solution is maintained at 11 to 12 by the simultaneous dropwise addition of 1N aqueous sodium hydroxide solution. After subsequently stirring for 1 hour, sufficient "Amberlite" IR 120 in the H+-form is added thereto to decrease the pH value to 1.4. After separating off the ion exchanger, the reaction mixture is poured into 1.7 liters acetone, the precipitated crystals are filtered off with suction, washed with acetone and dried. There are thus obtained 4.7 g. (89% of theory) of the disodium salt of 1-hydroxy-4-(N-phthaloylglycyl)-aminobutane-1,1-diphosphonic acid; m.p. 103° C. (decomp.: $M_{rel}=0.6$).

2 g. of the disodium salt of 1-hydroxy-4-(N-phthaloylglycyl)-aminobutane-1,1-diphosphonic acid are dissolved in 20 ml. water, mixed with 0.5 ml. glacial acetic acid and 0.9 ml. phenylhydrazine and stirred for 5 hours at 50° C. After cooling and separating of the precipitated phthaloylphenylhydrazide, the mixture is stirred in methanol, there being obtained 1.1 g. (68% of theory) of the desired compound in the form of the disodium salt; m.p. >300° C.; $M_{rel}=0.36$).

The following compounds are obtained in an analogous manner:

(a) by the reaction of 4-(N-methyl)-aminobutane-1-hydroxy-1,1-diphosphonic acid with phthaloylglycyl chloride and subsequent splitting off of the phthaloyl radical with water (as described in Example 2), there is obtained 4-(N-glycyl-N-methyl)-aminobutane-1-hydroxy-1,1-diphosphonic acid in a yield of 52% of theory; m.p. 205°-210° C. (decomp.); $M_{rel}=0.34$.

(b) by the reaction of 4-aminobutane-1-hydroxy-1,1-diphosphonic acid with phthaloylaminoisobutyric acid chloride (m.p. 78°-81° C.) and subsequent splitting off of the phthaloyl radical, there is obtained 4-(N-aminoisobutyryl)-aminobutane-1-hydroxy-1,1-diphosphonic acid in a yield of 12% of theory; m.p. 80° C. (decomp.); $M_{rel}=0.24$.

(c) by the reaction of 6-aminohexane-1-hydroxy-1,1-diphosphonic acid with phthaloylglycyl chloride and subsequent splitting off of the phthaloyl radical, there is obtained 6-(N-glycyl)-aminohexane-1-hydroxy-1,1-diphosphonic acid in a yield of 13% of theory; m.p. 165°-170° C. (decomp.); $M_{rel}=0.31$.

(d) by the reaction of 4-(N-glycylglycyl)-aminobutane-1-hydroxy-1,1-diphosphonic acid (see Example 3) with phthaloylglycyl chloride and subsequent splitting off of the phthaloyl radical, there is obtained 4-(N-glycylglycylglycyl)-aminobutane-1-hydroxy-1,1-diphosphonic acid in a yield of 6% of theory; m.p. 100°-103° C. (decomp.); $M_{rel}=0.21$.

EXAMPLE 2

The splitting off of phthalic acid from the N-phthaloylglycyl intermediate of Example 1 can be achieved by boiling for one hour 19 ml. of an aqueous solution of 1.9 g. 1-hydroxy-4-(N-phthaloylglycyl)-aminobutane-1,1-diphosphonic acid. After separating off the phthalic acid which precipitates out after cooling, the filtrate is evaporated and the residue is stirred up with methanol. There is thus obtained 1.0 g. (74% of theory) 4-(N-glycyl)-aminobutane-1-hydroxy-1,1-diphosphonic acid; m.p. 200° C. sintering/202°-204° C. (decomp.) after recrystallisation from methanol/water; $M_{rel}=0.36$.

EXAMPLE 3

4-(N-Glycylglycyl)-aminobutane-1-hydroxy-1,1-diphosphonic acid

From the 4-(N-glycyl)-aminobutane-1-hydroxy-1,1-diphosphonic acid compound described in Example 1, there is prepared in an analogous manner the N-phthaloylglycylglycyl compound (yield 65% of theory; m.p. above 96° C. sinters and slowly foams; $M_{rel}=0.55$).

The phthalyl radical is split off with phenylhydrazine in the manner described in Example 1. After separating off the precipitated phthaloylphenyl hydrazide, the filtrate is stirred into a 10 fold amount of methanol and the precipitated crystals are isolated, dissolved in water and acidified with an ion exchanger. The filtrate is evaporated and the residue is stirred with methanol. The desired product is thus obtained in a yield of 27% of theory; m.p. 122° C. sinters/170°-172° C. (decomp.); $M_{rel}=0.34$.

The following compounds are obtained in an analogous manner:

(a) by the reaction of the tetrasodium salt of 4-aminobutane-1-hydroxy-1,1-diphosphonic acid with phthaloyl-D-alanyl chloride, followed by acidification, there is obtained 1-hydroxy-4-(N-phthaloyl-D-alanyl)-aminobutane-1,1-diphosphonic acid (m.p. 113° C. sinters, 133°-136° C. (decomp.); $M_{rel}=0.59$) in a yield of 99% and from this, by splitting with phenylhydrazine, in a yield of 46%, 4-(N-D-alanyl)-aminobutane-1-hydroxy-1,1-diphosphonic acid (m.p. 117° C. (decomp.); $M_{rel}=0.37$).

(b) by the reaction of the tetrasodium salt of 4-aminobutane-1-hydroxy-1,1-diphosphonic acid with phthaloyl-L-alanyl chloride, followed by acidification, there is obtained 1-hydroxy-4-(N-phthaloyl-L-alanyl)-aminobutane-1,1-diphosphonic acid (m.p. 92° C. sinters, 137°-141° C. (decomp.); $M_{rel}=0.59$) in a yield of 97% and from this, by splitting with phenylhydrazine, in a yield of 53%, 4-(N-L-alanyl)-aminobutane-1-hydroxy-1,1-diphosphonic diphosphonic acid (m.p. 102° C. (decomp.); $M_{rel}=0.37$).

EXAMPLE 4

5-(N-Glycyl)-aminopentane-1-hydroxy-1,1-diphosphonic acid 6.06 g. 5-aminopentane-1-hydroxy-1,1-diphosphonic acid are placed into 80 ml. water and adjusted to pH 11 with 10N aqueous sodium hydroxide solution. A solution of 6.8 g. phthaloylglycyl chloride in 80 ml. methylene chloride is added dropwise thereto, with stirring, and the pH value is kept between 10 and 11 by the dropwise addition of 10N aqueous sodium hydroxide solution. After 3 hours, the phases are separated and the aqueous phase is extracted with methylene chloride and brought to a pH of 5 with 2N hydrochloric acid. The solution is mixed with 350 ml. methanol and stirred for several hours, while cooling with ice. There are obtained 6.7 g. (65% of theory) of the disodium salt of 1-hydroxy-5-(N-phthaloylglycyl)-aminopentane-1,1-diphosphonic acid; m.p. >300 ° C.; $M_{rel}=0.55$).

3.07 g. of this disodium salt are dissolved in 30 ml. water, mixed with 1.27 g. phenylhydrazine and 720 mg. acetic acid and heated to 50° C. for 30 hours. After cooling, the precipitate is filtered off with suction and the filtrate is treated with active charcoal and slowly mixed with 90 ml. methanol. Stirring is continued for 1 hour with ice cooling and the precipitate is filtered off with suction. There is obtained 1.6 g. (70% of theory) of the monosodium salt of 5-(N-glycyl)-aminopentane-1-hydroxy-1,1-diphosphonic acid; m.p. ≈250° C. (decomp.); $M_{rel}=0.40$).

The following compounds are obtained in an analogous manner:

(a) by the reaction of 5-aminopentane-1-hydroxy-1,1-phosphonate with phthaloyl-D,L-alanyl chloride, there is obtained the disodium salt of 1-hydroxy-5-(N-phthaloyl-D,L-alanyl)-aminopentane-1,1-diphosphonic acid (m.p. >300° C.; $M_{rel}=0.60$) in a yield of 65% of theory and from this, by splitting with phenylhydrazine, in a yield of 52% of theory, the monosodium salt of 5-(N-D,L-alanyl)-aminopentane-1-hydroxy-1,1-diphosphonic acid; m.p. ≈270° C. (decomp.); $M_{rel}=0.38$.

(b) by the reaction of 5-amino-1-hydroxy-1,1-diphosphonic acid with phthaloyl-β-alanyl chloride, there is obtained the disodium salt of 1-hydroxy-5-(N-phthaloyl-β-alanyl)-aminopentane-1,1-diphosphonic acid (m.p. > 300° C.; $M_{rel}=0.60$) in a yield of 50% of theory and from this, by splitting with phenyl hydrazine, in a yield of 59% of theory, the monosodium salt of 5-(N-β-alanyl)-aminopentane-1-hydroxy-1,1-diphosphonic acid; m.p. 260° C. (decomp.); $M_{rel}=0.35$.

EXAMPLE 5

5-(N-Glycyl)-aminopentane-1-hydroxy-1,1-diphosphonic acid 0.75 g. 5-Aminopentane-1-hydroxy-1,1-diphosphonic acid disodium salt are dissolved in 50 ml. water and mixed with 0.21 g. sodium hydrogen carbonate Subsequently, while stirring, there is added 1.53 g. N-benzyloxycarbonylglycine N-hydroxysuccinimide ester in 10 ml. dimethoxyethane, the pH value of the solution being kept between 7.0 and 7.5 by the addition of solid sodium hydrogen carbonate. After 1 hour, insoluble material is filtered off and the filtrate is adjusted to a pH of 5 with 2N hydrochloric acid and mixed with 300 ml. methanol. The mixture is cooled, the precipitate is filtered off with suction and there is obtained 0.92 g. (about 71% of theory) 5-(N-benzyloxycarbonylglycyl)-aminopentane-1-hydroxy-1,1-diphosphonic acid as the sodium salt; m.p. > 300° C.; $M_{rel}=0.58$).

This 0.92 g. of sodium salt is dissolved in 70 ml. water/35 ml. ethanol, 1 g. palladium on charcoal (10%) is added thereto and hydrogenation is carried out at normal pressure and at ambient temperature. After completion of the take up of hydrogen, the catalyst is filtered of with suction and the filtrate is mixed with 300 ml. acetone. The precipitate is filtered off with suction to give 0.41 g. (about 50% of theory) 5-(N-glycyl)-aminopentane-1-hydroxy-1,1-diphosphonic acid as the disodium salt; m.p. 240° C., sinters, 285° C. (decomp.); $M_{rel}=0.40$.

The following compounds are obtained in an analogous manner:

(a) by the reaction of 5-aminopentane-1-hydroxy-1,1-diphosphonic acid with N-benzyloxycarbonyl-L-alanine N-hydroxysuccinimide ester and subsequent hydrogenation, there is obtained 5-(N-L-alanyl)-aminopentane-1-hydroxy-1,1-diphosphonic acid as the disodium salt in a yield of 73% of theory; m.p. > 300° C.; $M_{rel}=0.38$; $[\alpha]_D^{20}=+16.1°$, c=2.5 in water.

(b) by the reaction of 5-aminopentane-1-hydroxy-1,1-diphosphonic acid with N-benzyloxycarbonyl-D-alanine N-hydroxysuccinimide ester and subsequent hydrogenation, there is obtained 5-(N-D-alanyl)-aminopentane-1-hydroxy-1,1-diphosphonic acid as the disodium salt in a yield of 68%; m.p. > 300° C.; $M_{rel}=0.38$; $[\alpha]_D^{20}=-15.8°$, c=2.5 in water.

(c) by the reaction of 3-aminopropane-1-hydroxy-1,1-diphosphonic acid with N-benzyloxycarbonylglycine N-hydroxysuccinimide ester and subsequent hydrogenation, there is obtained 3-(N-glycyl)-aminopropane-1-hydroxy-1,1-diphosphonic acid in a yield of 56%; m.p. 120° C., sinters, 155°-160° C.; $M_{rel}=0.42$.

(d) by the reaction of 3-aminopropane-1-hydroxy-1,1-diphosphonic acid with N-benzyloxycarbonyl-L-alanine N-hydroxysuccinimide ester and subsequent hydrogenation, there is obtained 3-(N-L-alanyl)-aminopropane-1-hydroxy-1,1-diphosphonic acid as the disodium salt in a yield of 52% of theory; m.p. > 300° C.; $M_{rel}=0.35$; $[\alpha]_D^{20}=+13.2°$, c=2.5 in water.

(e) by the reaction of 3-aminopropane-1-hydroxy-1,1-diphosphonic acid with N-benzyloxycarbonyl-D-alanine N-hydroxysuccinimide ester and subsequent hydrogenation, there is obtained 3-(N-D-alanyl)-aminopropane-1-hydroxy-1,1-diphosphonic acid as the disodium salt in a yield of 57% of theory; m.p. > 300° C.; $M_{rel}=0.35$; $[\alpha]_D^{20}=-13.7°$, c=2.5 in water.

(f) by the reaction of 3-aminopropane-1-hydroxy-1,1-diphosphonic acid with N-benzyloxycarbonyl-L-proline N-hydroxysuccinimide ester and subsequent hydrogenation, there is obtained 3-(N-L-prolyl)-aminopropane-1-hydroxy-1,1-diphosphonic acid as the disodium salt in a yield of 21% of theory; m.p. > 300° C.; $M_{rel}=0.20$.

(g) by the reaction of 5-aminopentane-1-hydroxy-1,1-diphosphonic acid with N-benzyloxycarbonyl-L-proline N-hydroxysuccinimide ester and subsequent hydrogenation, there is obtained 5-(N-L-prolyl)-aminopentane-1-hydroxy-1,1-diphosphonic acid as the disodium salt in a yield of 52% of theory; m.p. > 300° C.; $M_{rel}=0.38$.

(h) by the reaction of 5-aminopentane-1-hydroxy-1,1-diphosphonic acid with N-benzyloxycarbonylglycylglycine N-hydroxysuccinimide ester (m.p. 155°-158° C.) and subsequent hydrogenation, there is obtained 5-(N-glycylglycyl)-aminopentane-1-hydroxy-1,1-diphosphonic acid as the disodium salt in a yield of 54% of theory; m.p. > 300° C.; $M_{rel}=0.32$.

(i) by the reaction of 3-aminopropane-1-hydroxy-1,1-diphosphonic acid with N-benzyloxycarbonyl-L-alanyl-L-alanine N-hydroxysuccinimide ester (m.p. 150°-153° C.) and subsequent hydrogenation, there is obtained 3-(N-L-alanyl-L-alanyl)-aminopropane-1-hydroxy-1,1-diphosphonic acid as the disodium salt in a yield of 14% of theory; m.p. > 300° C.; $M_{rel}=0.25$.

(j) by the reaction of 4-aminobutane-1-hydroxy-1,1-diphosphonic acid with N-benzyloxycarbonyl-L-proline N-hydroxysuccinimide ester and subsequent hydrogenation, there is obtained 4-(N-L-prolyl)-aminobutane-1-hydroxy-1,1-diphosphonic acid in a yield of 45% of theory: m.p. 75° C. (decomp.); $M_{rel}=0.20$.

(k) by the reaction of 4-aminobutane-1-hydroxy-1,1-diphosphonic acid with N-benzyloxycarbonylsarcosine N-hydroxysuccinimide ester and subsequent hydrogenation, there is obtained 4-(N-sarcosyl)-aminobutane-1-hydroxy-1,1-diphosphonic acid in a yield of 50% of theory; m.p. 97°-101 ° C. (decomp.); $M_{rel}=0.26$.

EXPERIMENTAL TESTING

Male Wistar rats from our own breeding weighing about 160 g were thyroparathyroidectomixed on day 1. On day 5, the success of the operation was controlled by measuring calcemia after a night fasting. From that day on, all the animals were group-fed, that all of them ate the same quantity of food. Furthermore, the animals then received daily for 3 days, 2 subcutaneous injections, one containing 25 ug of a synthetic retinoid, the other one the bisphosphonate to be tested. Additionally, all animals were given 2 ug of thyrozine the first and last day of treatment. 24 hours after the last injection of the retinoid and the biphosphonates and after one night fasting, blood was taken by retroorbital puncture under ether anesthesia. Plasma calcium was then analyzed by means of atomic absorption.

The bisphosphonates were given first at a dose of 0.1 mg P/kg in a volume of 2 ml/kg, the less active also at 1 and 10 mg P/kg.

The table shows the various doses compared with 1-hydroxyethane-1.1-diphosphonate acid of Patent Specification No. 18 13 659 (Fed. Rep. Germany).

TABLE

| Example | mg P/kg | | | |
|---|---|---|---|---|
| | 0.01 | 0.1 | 1.0 | 10 |
| 1-Hydroxy-ethane-1,1-diphosphonic acid | 0 | 0 | 0 | (+) |
| 1 | 0 | + | ++ | |
| 1 c | 0 | + | ++ | |
| 1 d | 0 | 0 | (+) | ++ |
| 2 | 0 | + | ++ | |
| 3 | 0 | 0 | + | +++ |
| 3 a | 0 | 0 | ++ | 0 |
| 3 b | (+) | ++ | +++ | |
| 4 | 0 | (+) | + | + |
| 4 a | 0 | 0 | +++ | ++ |
| 5 | 0 | (+) | + | + |
| 5 a | (+) | + | +++ | |
| 5 b | 0 | (+) | (+) | 0 |
| 5 c | 0 | ++ | + | |
| 5 e | 0 | (+) | (+) | 0 |
| 5 f | 0 | (+) | + | 0 |
| 5 k | 0 | 0 | +++ | + |

0 = Depression of Hypercalcaemie −0.99 to 0.99 mg %
(+) = Depression of Hypercalcaemie 1.0 to 1.99 mg %
+ = Depression of Hypercalcaemie 2.0 to 2.99 mg %
++ = Depression of Hypercalcaemie 3.0 to 3.99 mg %
+++ = Depression of Hypercalcaemie >4.0 mg %

It will be understood that the specification and examples are illustrative but not limitative of the present invention and that other embodiments within the spirit and scope of the invention will suggest themselves to those skilled in the art.

What is claimed is:

1. A diphosphonic acid derivative compound of the formula $$\begin{array}{c} R_1 \\ \diagdown \\ N-X-C-(N-Y-C)_n-N-Z-C-A \\ \diagup \quad \| \quad | \quad \| \quad | \quad | \\ R_2 \quad O \quad R_3 \quad O \quad R_4 \quad P(OR_5)_2 \\ \qquad\qquad\qquad\qquad\qquad \| \\ \qquad\qquad\qquad\qquad\qquad O \end{array} \quad (I)$$

with $P(OR_5)_2$ (=O) also at top of central C, wherein $R_1$, $R_2$, $R_3$, $R_4$ and $R_5$, are individually selected from the group consisting of hydrogen and $C_1$-$C_4$ lower alkyl. $R_1$ and X or $R_3$ and Y or $R_4$ and Z, together with the nitrogen atom to which they are attached, can form a five-or six-membered ring, X and Y, which can be the same or different, represent a straight- or branched alkylene chain with up to 6 carbon atoms which is unsubstituted or is substituted once by phenyl, imidazolyl or indolyl, Z is a straight-chained or branched alkylene chain with up to 6 carbon atoms and which is uninterrupted or interrupted once by Oxygen or sulphur and which is unsubstituted or substituted once by phenyl, hydroxyl, or a pharmacologically acceptable salt thereof.

or a pharmacologically acceptable salt thereof.

2. The compound of claim 1, wherein A is hydroxyl, n is 0 or 1, $R_4$ and $R_5$ are hydrogen, Z is a straight-chained alkylene chain with 2 to 5 carbon atoms, the grouping $(R_1,R_2)$—N—X—CO— is glycyl, alanyl, prolyl or sarcosyl and the grouping —N($R_3$)—Y—CO—is glycyl or alanyl.

3. The compound of claim 1 wherein the substituents for X,Y and Z are individually selected from the group consisting of phenyl, imidazolyl and indolyl, and Z is a straight-chained alkylene chain with up to 6 carbon atoms.

4. The compound of claim 3 wherein $R_1$, $R_2$, $R_3$ and $R_4$ are individually selected from the group consisting of hydrogen, methyl, ethyl and isopropyl, and $R_5$ is hydrogen.

5. The compound of claim 1 wherein $R_1$, $R_2$, $R_3$ and $R_4$ are individually selected from the group consisting of hydrogen, methyl, ethyl and isopropyl, and $R_5$ is hydrogen.

6. The compound of claim 1 designated 4-(N-L-alanyl)-aminobutane-1-hydroxy-1,1-diphosphonic acid or the mono- or disodium salt thereof.

7. The compound of claim 1 designated 5-(N-D,L-alanyl)-aminopentane-1-hydroxy-1, 1-diphosphonic acid or the mono- or disodium salt thereof.

8. The compound of claim 1 designated 5-(N-, L-alanyl)-aminopentane-1-hydroxy-1, 1-diphosphonic acid or the mono- or disodium salt thereof.

9. The compound of claim 1 designated 4-(N-sarcosyl)-aminobutane-1-hydroxy-1, 1-diphosphonic acid the mono- or disodium salt thereof.

10. The compound of claim 1 in the form of a mono- or dialkali metal salt or a ammonium salt.

11. A pharmaceutical composition for treatment of calcium metabolism disturbances comprising an effective amount of the compound of claim 1 in a pharmaceutically acceptable carrier.

12. The pharmaceutical composition of claim 11 containing 1 to 1000 mg of the compound of claim 1.

13. The pharmaceutical composition of claim 11 wherein the compound is
4-(N- L-alanyl)-aminobutane -1-hydroxy-1, 1-diphosphonic acid or the mono- or disodium salt thereof or
5-(N-D, L-alanyl)-aminopentane-1-hydroxy-1, 1-diphosphonic acid or the mono- or disodium salt thereof or
5-(N-L-alanyl)-aminopentane-1-hydroxy-1, 1-diphosphonic acid or the mono- or disodium salt thereof or
4-(N-sarcosyl)-aminobutane-1-hydroxy-1, 1-diphosphonic acid the mono- or disodium salt thereof.

14. A method for the treatment of calcium metabolism disturbances comprising administering an effective amount of the compound of claim 1.

15. The method of claim 14 wherein 1 to 1000 mg of the compound are administered.

16. The method of claim 15 wherein 10 to 200 mg of the compound are administered.

17. The method of claim 15 wherein 1 to 100 mg of the compound are administered.

18. A method for the treatment of calcium metabolism disturbances comprising administering an effective amount of the pharmaceutical composition of claim 13.

* * * * *

UNITED STATES PATENT AND TRADEMARK OFFICE
CERTIFICATE OF CORRECTION

PATENT NO. : 4,666,895

DATED : May 19, 1987

INVENTOR(S) : Elmar Bosies, Rudi Gall

It is certified that error appears in the above-identified patent and that said Letters Patent is hereby corrected as shown below:

Column 1, line 43, formula I, that portion of the formula reading

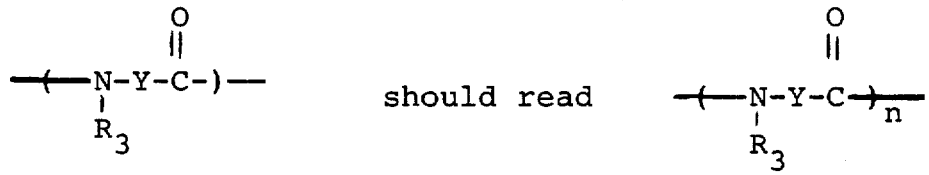

Column 8, delete lines 44-47; and insert --4-N-(Glycyl)-amino-butane-1-hydroxy-1,1-diphosphonic acid--.
Column 10, line 21, delete one instance of "diphosphonic".
Column 13, Claim 1, line 54, insert before "hydroxyl," --imidazolyl or indolyl, $\underline{n}$ is 0, 1 or 2 and A is hydrogen or--;
line 56, delete "or a pharmacologically acceptable salt thereof.".

Signed and Sealed this

Tenth Day of May, 1988

Attest:

DONALD J. QUIGG

Attesting Officer      Commissioner of Patents and Trademarks